United States Patent
Seissler

(10) Patent No.: US 6,491,430 B1
(45) Date of Patent: Dec. 10, 2002

(54) MOBILE X-RAY APPARATUS AND METHOD FOR DETERMINING PROJECTION GEOMETRIES THEREIN

(75) Inventor: Wolfgang Seissler, Uttenreuth (DE)

(73) Assignee: Siemens Aktiengesellschaft, Munich (DE)

(*) Notice: Subject to any disclaimer, the term of this patent is extended or adjusted under 35 U.S.C. 154(b) by 65 days.

(21) Appl. No.: 09/630,967

(22) Filed: Aug. 2, 2000

(30) Foreign Application Priority Data

Aug. 3, 1999 (DE) .......................................... 199 36 408

(51) Int. Cl.[7] .............................................. G01D 18/00
(52) U.S. Cl. ............................ 378/207; 378/18; 378/20; 378/198; 378/205; 378/207
(58) Field of Search ............................ 378/18, 20, 198, 378/205, 207

(56) References Cited

U.S. PATENT DOCUMENTS

| | | | |
|---|---|---|---|
| 4,053,780 A | 10/1977 | Sparks | 378/14 |
| 4,907,157 A | 3/1990 | Uyama et al. | 382/131 |
| 5,014,293 A | 5/1991 | Boyd et al. | 378/197 |
| 5,436,950 A | 7/1995 | Pauli et al. | 378/4 |
| 5,442,674 A * | 8/1995 | Picard et al. | 378/20 |
| 5,706,324 A | 1/1998 | Wiesent et al. | 378/4 |
| 5,822,396 A | 10/1998 | Navab et al. | 378/207 |
| 5,835,563 A | 11/1998 | Navab et al. | 378/207 |
| 5,917,881 A * | 6/1999 | Jeffery | 378/98.8 |
| 5,923,727 A * | 7/1999 | Navab | 378/207 |
| 6,031,891 A * | 2/2000 | Roos et al. | 378/98.2 |
| 6,044,132 A * | 3/2000 | Navab | 378/163 |
| 6,092,928 A * | 7/2000 | Mattson et al. | 378/205 |
| 6,120,180 A | 9/2000 | Graumann | 378/206 |
| 6,139,183 A * | 10/2000 | Graumann | 378/206 |
| 6,206,566 B1 * | 3/2001 | Schuetz | 378/205 |

* cited by examiner

Primary Examiner—Robert H. Kim
Assistant Examiner—Allen C. Ho
(74) Attorney, Agent, or Firm—Schiff Hardin & Waite

(57) ABSTRACT

In a mobile X-ray apparatus and a method for determining projection geometries therein, an X-ray system, including an X-ray source and a planar X-ray detector, is provided which is displaceable relative to an examination subject by a displacement arrangement for obtaining a series of 2D projections which are used to construct a 3D image of the subject. Each 2D projection has a projection geometry associated therewith. The X-ray system and the displacement arrangement exhibit mechanical instabilities, due to the light weight construction necessary for mobility of the apparatus, which would preclude accurate identification of the 2D projection geometries. The displacement arrangement therefore includes components for assuring a reproducible displacement movement of the X-ray system, so that projection geometries for respective positions of the X-ray system can be identified in advance, in a calibration procedure, allowing offline determination of the projection geometries.

9 Claims, 1 Drawing Sheet

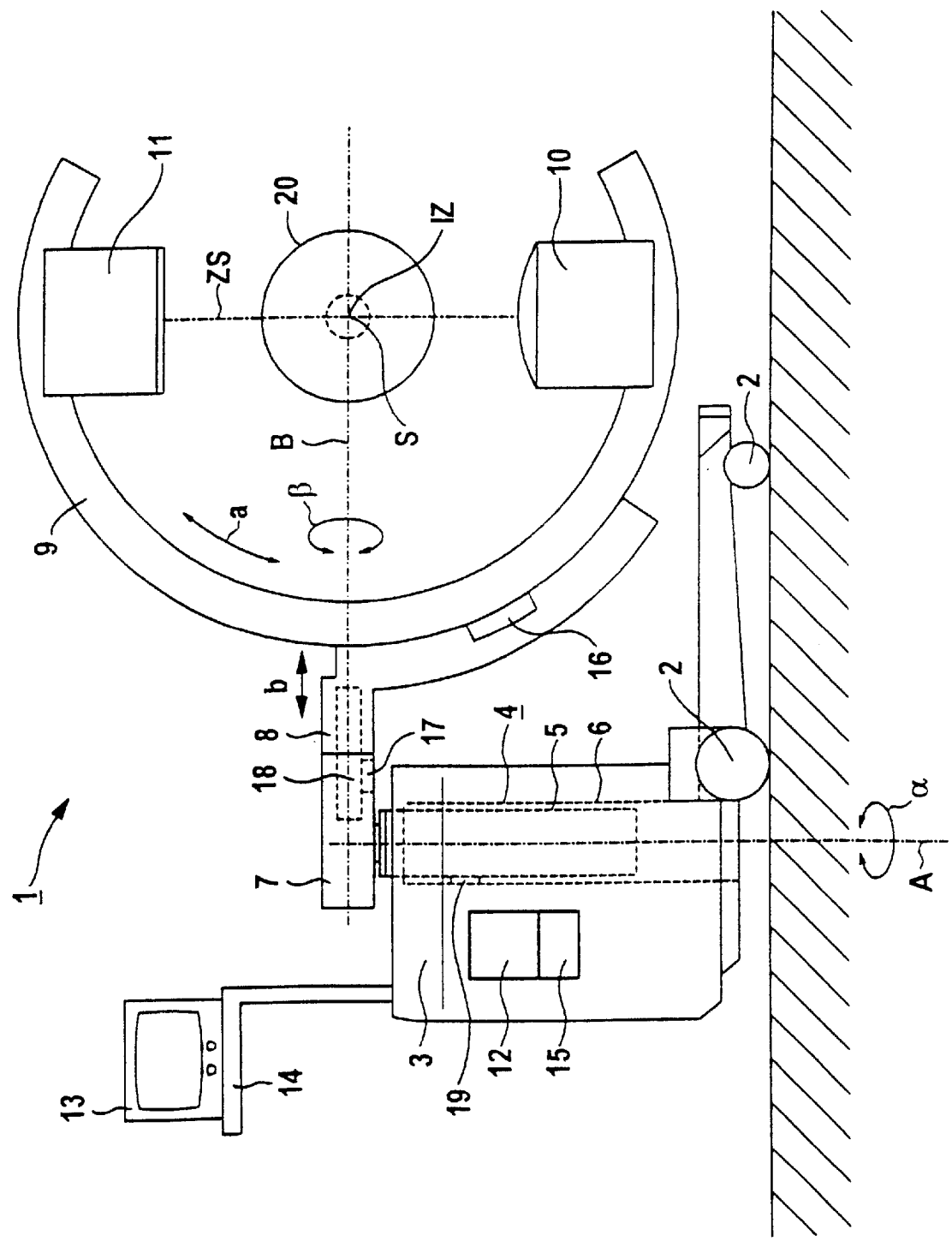

MOBILE X-RAY APPARATUS AND METHOD FOR DETERMINING PROJECTION GEOMETRIES THEREIN

BACKGROUND OF THE INVENTION

1. Field of the Invention

The present invention relates to a mobile X-ray device of the type having an X-ray system including an X-ray source and a planar X-radiation detector, the X-ray system being displaceable relative to the subject for picking up series of 2D projections of a subject for a reconstruction of at least one 3D image of the subject. Further, the invention relates to a method for determining projection geometries for such an X-ray device.

2. Description of the Prior Art

X-ray devices of the aforementioned type are used, for example, in the medical field to reconstruct 3D images of a body part from a series of picked up 2D projections of the body part of a patient. The projection geometries, i.e., the positions of the X-ray source and of the X-ray detector, as well as the projection angle with respect to each of the individual 2D projections of the series, must be known in order to reconstruct accurate 3D images from the 2D projections that are picked up by the X-ray system.

U.S. Pat. No. 4,053,780 discloses an axially operating, room mounted tomographic scanning device with an X-ray system that has an X-ray source and an X-ray detector, this X-ray system being attached to a frame and being displaceable relative to the subject for picking up projections of the subject. Further, the scanning device has means for displacing the X-ray system, which means, in a calibration process, allow the determination of data required for purposes of reconstructing an image.

German PS 35 31 741 describes a tomography device with a movable system for generating radiation and with a movable radiation measuring system that can be set up independently of the position of the radiation generating system.

U.S. Pat. No. 5,014,293 describes an X-ray computed tomography device with a device cart and with an X-ray system, which is arranged at the C-arm of the device cart. The X-ray system has an X-ray source that emits a fan-shaped X-ray bundle and an X-ray detector in the form of a detector array. For acquiring X-ray pickups, the C-arm can be moved around a subject, whereby the fan-shaped X-ray bundle penetrates the subject an strikes on the detector array. 3D images of the subject can be acquired from the X-ray pickups.

German PS 43 35 300 describes a computer tomography device with an X-ray system and a measuring means for the position of the center of rotation, which measuring means controls a focus deviation unit in the sense of a guidance of the focus given a displacement of the center of rotation.

German OS 197 46 093 discloses a movable X-ray device of the type initially described, wherein transmission and reception devices for sound waves or electromagnetic waves are provided, which allow the detection of projection geometries during the pickup of a series of 2D projections.

German PS 195 12 819 describes an X-ray computed tomography device, wherein, during the pickup of 2D projections, X-ray-positive markers are arranged in the measuring field above and below the area of the subject to be examined. The markers are imaged in the 2D projections. The projection geometries can be detected for each 2D projection by evaluating the 2D projections.

In the last two cited known X-ray devices in particular, online detection of the projection geometries is used, namely detection of the projection geometries during the pickup of a series of 2D projections of a subject, or at least during the recording of data during the pickup of a series of 2D projections, which allow the detection of the projection geometries. Such online detection is necessary in these devices, since the X-ray devices are mechanically unstable with respect to the displacement movement of the X-ray system because, being mobile, a lighter structure must be used (as opposed to the heavier, and thus more stable, structure which can be used in a non-mobile device). These mechanical instabilities rule out an exactly reproducible displacement movement of the X-ray system, so that the positions of the X-ray source and the X-ray receiver, at the respective point in time of the pickup of a 2D projection by means of, for example, locators or position transmitters that are present in the X-ray devices, cannot be exactly determined such that 3D images of high quality could be reconstructed.

Online detection of the projection geometries, however, requires the use of a large amount of computing power in order to, in a desired way, arrive at 3D images of the subject in an optimally short time after the series of 2D projections have been picked up. Therefore, realtime reconstruction of 3D images is only possible when expensive computers with high computing power are utilized.

SUMMARY OF THE INVENTION

An object of the present invention is to provide the projection geometries, which are necessary for reconstructing 3D images, in a simplified way for a movable X-ray device.

This object is inventively achieved in a mobile X-ray device with an X-ray system that includes an X-ray source and a planar X-ray detector, the X-ray system being displaceable relative to the subject for picking up a series of 2D projections of a subject for reconstruction of at least one 3D image of the subject and which has a displacement arrangement for assuring a reproducible displacement movement of the X-ray system by means of which the projection geometries of the X-ray system required for the reconstruction of a 3D image are determined in a calibration process prior to the pickup of series of 2D projections of the subject. As a result of the displacement arrangement which assures a reproducible displacement movement of the X-ray system, it is possible to determine the projection geometries prior to the pickup of series of 2D projections of a subject in a (normally) onetime calibration process. Thus, the once detected projection geometries can be repeatedly used for reconstructing 3D images from series of 2D projections of different subjects picked up at different points in time, which hitherto has been regarded as impossible with respect to mobile X-ray devices due to the light construction necessary for mobility and the instabilities associated therewith. The realization of an offline determination of the projection geometries, namely a determination of the projection geometries prior to the actual pickup of 2D projections of a subject, is based on the recognition that the twists of the C-arm—which occur when the X-ray system arranged at the C-arm is displaced—can be considered as mechanical constants; these twists leading to deviations of the X-ray system from its ideal displacement movement, which can be detected by means of locators. Under equal conditions guaranteed by the drive for the displacement of the C-arm, this assumption proves sufficiently correct, so that the displacement movement of the C-arm or X-ray system can be regarded as reproducible.

In an embodiment of the invention the displacement arrangement has a digitally controlled drive, which effects the displacement movement of the X-ray system. The digitally controlled drive preferably is a software-controlled drive, and can be a pulse motor according to an embodiment of the invention, and makes a precise displacement of the X-ray system possible. The pulse motor cooperates, for example, with the C-arm, which accepts the X-ray system. Thus, individual positions can be repeatedly reached in an accurate manner within 500 $\mu°$ in the displacement movement of the X-ray system, so that the positions of the X-ray source and the X-ray detector identified during the calibration can be almost exactly achieved again with respect to later displacement processes of the X-ray system. Thus, the conditions that are present for later measurements with regard to the mechanical constants of the X-ray system correspond to the conditions that are present during the calibration.

According to a version of the invention, the X-ray system is arranged at a carrying device borne by a support which is displaceable along an axis in a holding device and which is pivotably arranged for rotation around the axis relative to the holding device, and the displacement arrangement include compensation components, which exhibit a defined effective direction and which compensate any mechanical play that is present between the support and the holding device.

In a further version of the invention the holding device, in a height-adjustable manner, is arranged at a lifting device having at least two elements that can be moved relative to one another, these elements forming additional compensation components, which exhibit a defined effective direction and which compensate any mechanical play that is present between the elements of the lifting device.

The compensation components can be locking components, for example, such as springs or spring-biased locking pins, which, during the calibration process and during later measuring processes, clamp the support against the holding device, or clamp, the elements of the lifting device against one another, in a defined effective direction, so that equal conditions always exist with respect to different measuring processes.

According to an embodiment of the invention, the carrying device for the X-ray system is a C-arm.

The above object also is achieved in an inventive method for the offline determination of the projection geometries for a movable X-ray device, wherein the X-ray system of the X-ray device is arranged at a carrying device, which is held in a support and which is displaceable relative to the support, and wherein the support can be pivoted relative to a holding device around an axis extending through the support and the holding device and/or wherein the support, along the axis, is displaceably arranged at the holding device and/or wherein the holding device is height-adjustably arranged at a lifting device. The inventive method includes the following steps:

a) adjusting a first pivot position of the support relative to the holding device and/or a first position of the support relative to the holding device along the axis and/or a first height adjustment of the holding device, b) arranging a phantom, which is provided for determining the projection geometries, relative to the X-ray system such that it can be penetrated by an X-ray bundle proceeding from the X-ray source to the X-ray detector, c) picking up a series of 2D projections of the phantom by displacing the carrying device in the support, d) evaluating the 2D projections of the phantom for detecting (identifying) the projection geometries for each of the 2D projections, e) storing the projection geometries for the selected position of the support and/or the holding device, and f) repeating the steps a) through e) if and when the position of the support and/or the holding device changes.

The inventive method makes it possible, in a simple way, to detect projection geometries prior to an examination of a subject for all desired displacement movements or adjustments of the X-ray system relative to a subject and makes it possible to have these projection geometries available for later subject measurements, or for the reconstruction of 3D images from measured 2D projections of a subject. Normally, as far as the construction of the X-ray device does not change, the calibration must be undertaken only once. Therefore, a computerized online determination of projection geometries for reconstructing 3D images from a series of 2D projections is no longer necessary.

DESCRIPTION OF THE DRAWINGS

An exemplary embodiment of the invention is shown in the single schematic FIGURE, which shows an inventive mobile X-ray apparatus.

DESCRIPTION OF THE PREFERRED EMBODIMENTS

The inventive X-ray apparatus shown in the FIGURE is a C-arm X-ray apparatus 1 with a device cart 3 that can be moved on wheels 2. The C-arm X-ray apparatus 1 has a telescoping column 4 (indicated in broken lines in the FIGURE) with two elements 5, 6 (in this present exemplary embodiment). The element 5 can be vertically displaced relative to the element 6 and can be rotated around a longitudinal axis A of the telescoping column 4 in the direction of the double arrow α. A holding device 7 is arranged at the telescoping column 4; a support 8 for supporting a C-arm 9 is, in turn, arranged at the holding part 7. The C-arm 9 is provided with an X-ray system, which includes an X-ray source 10 and a planar X-ray detector 11. The X-ray source 10 and the X-ray detector 11, at the ends of the C-arm 9, are arranged opposite one another such that a central beam ZS of a conical X-ray bundle originating from the X-ray source 10 is incident approximately centrally on the X-ray detector 11.

The C-arm 9, in the exemplary embodiment, is supported by the support 8 so as to be isocentrally displaceable in the direction of the double arrow a along its circumference in a motor-driven manner. The support part 8 can be pivoted around a common axis B of the holding device 7 and the support 8 (compare double arrow β indicating angulation) and is displaceable at the holding device 7 in the direction of the axis B (compare double arrow b). The C-arm 9, which is connected to the telescoping column 4 via the support 8 and the holding device 7, is vertically displaceable relative to the device cart 3 by means of the telescoping column 4.

The C-arm X-ray apparatus 1 is provided for generating 3D images of a subject (not shown in the FIGURE). The 3D images are reconstructed by an image computer 12 given the 2D projections of the subject picked up from different projection angles, these 2D projections being acquired with the X-ray system formed by the X-ray source 10 and the X-ray detector 11. These 3D images can be displayed at a display unit 13, which is arranged on a holding device 14 of the C-arm X-ray apparatus 1.

For picking up 2D projections respectively at different projection angles, the C-arm 9 accepting the X-ray system is displaced along its circumference in the direction of the double arrow a within an angle range of approximately 200°, in a motor-driven manner around the subject to be examined and to be displayed in the 3D image. The X-ray system picks up approximately 50 to 100 2D projections of the subject during this displacement movement.

As explained above, it is necessary to know the projection geometries, namely the position of the X-ray source 10 and the X-ray detector 11, relative to the subject and it is required to know the projection angles for each of the 2D projections in order to reconstruct 3D images.

In the inventive C-arm X-ray apparatus 1, these projection geometries of a subject are detected in a calibration process prior to the pickup of the series of 2D projections and are kept ready for the later reconstruction of 3D images from picked up series of 2D projections of different subjects.

Such a course of action is only possible when the displacement movement of the X-ray system is reproducible. In order to assure this with respect to movable X-ray devices (which, per se, are mechanically unstable as a result of their necessary light construction guaranteeing mobility, so that a reproducibility of the displacement movement of the X-ray system is ruled out) in accordance with the invention a displacement arrangement provided at the C-arm X-ray apparatus 1. The displacement arrangement fashioned such that reproducibility of the displacement movements of the X-ray system is achieved and such that a weight increase of the X-ray device is mostly avoided, so that the mobility and therefore the easy handling of the C-arm X-ray apparatus 1 are not impaired.

The displacement arrangement includes a digitally software-controlled drive in the form of a pulse motor 16, which effects the displacement movement of the C-arm 9 relative to the support 8. The pulse motor 16 can be driven such that individual positions of the C-arm 9 can be repeatedly reached within 500 $\mu°$.

In the exemplary embodiment, the arrangement for reproducible displacement movements of the X-ray system also includes first compensation components, which, in the exemplary embodiment, are a spring-biased locking pin 17, which cooperates with a guide rod 18. The guide rod 18 is firmly connected to the support 8 and (in a way that is not shown in detail) can glide in a fitting of the holding device 7 in the direction of the axis B. In the exemplary embodiment, the guide rod 18 is arranged such that the axis B proceeds through the guide rod 18. Therefore, the support 8 can be displaced by the guide rod 18 relative to the holding device 7 along the axis B and can also be pivoted relative to the holding device 7 around the axis B.

When a desired position of the support 8 and therefore of the C-arm 9 relative to the holding device 7 is reached, a positive locking or clamping of the support 8 against the holding device 7 can ensue by operating the spring-biased locking pin 17 in a defined effective direction with operating means (not shown in detail). This locking or clamping compensates or eliminates any mechanical play that is normally present between the support 8 and the holding device 7, or between the guide rod 18 and the fitting.

Second compensation components, which can be a spring-biased locking pin 19 as well, cooperate with the two elements 5, 6 of the telescoping column 4 such that the movable element 5 can be fixed in a defined effective direction relative to the stationary element 6 given an arbitrary height adjustment of the telescoping column 4. Thus, the mechanical play that is normally present between the elements 5 and 6 during measuring processes with the X-ray system can be compensated or eliminated.

The two spring-biased pins 17 and 19 are respectively arranged such that the force needed for the locking is optimally small, so that the mechanical outlay associated with these compensation components is low.

The offline determination of the projection geometries ensues such that, as already described, a first adjustment of the support 8 or of the C-arm 9 is initially undertaken along the axis B and around the axis B relative to the holding device 7 and such that a first height adjustment of the holding device 7 is undertaken by displacing the elements 5, 6 of the telescoping column 4 relative to one another. For determining the projection geometries, a phantom 20 that is provided with X-ray-positive markers is arranged relative to the X-ray system such that an X-ray bundle proceeding from the X-ray source 10 to the X-ray detector 11 can at least partially penetrate the phantom 20. The phantom 20 can be a marker ring, for example, which is known from U.S. Pat. No. 5,822,396 or from U.S. Pat. No. 5,835,563 and which is actually provided for the online determination of projection geometries.

For example, when the phantom 20 is a marker ring exhibiting a center axis (as known from the above-cited patents) or a different phantom exhibiting a center axis, the phantom 20 is preferably positioned relative to the X-ray system such that the center axis of the phantom is at least essentially parallel to a system axis S of the C-arm X-ray apparatus 1 or coincides with the system axis S. The system axis S is the axis around which the X-ray system can be pivoted and proceeds through the isocenter IZ of the C-arm 9, and is substantially perpendicular to the axis B that also proceeds through the isocenter IZ and which is substantially perpendicular to the central beam ZS.

After the phantom 20 has been positioned relative to the X-ray system, a series of 2D projections of the phantom 20 are prepared, as the C-arm 9 is displaced by means of the pulse motor 16 in the circumferential direction, namely in the direction of the double arrow a. The projection geometries, with the aid of the image computer 12, for example, are detected by evaluating the 2D projections of the phantom 20 and are stored in the storage unit 15 dependent on the height adjustment of the holding device 7 and the position of the support 8 relative to the holding device 7. Further series of 2D projections are prepared as needed in the course of the calibration process for further adjustments of the holding device 7 and of the support 8 relative to the holding device 7, which adjustments deviate from the adjustment shown in the FIGURE. The projection geometries are determined for the individual 2D projections on the basis of the 2D projections and are deposited in the storage unit 15.

Thus, data sets of projection geometries appertaining to specific positions of the holding device 7 and of the support 8 are obtained, and the data sets are utilized for reconstructing 3D images from a series of 2D projections picked up from a subject given later corresponding adjustments of the holding device 7 and the support 8. It is thereby possible, with the aid of the pulse motor 16, to almost exactly reach the positions of the C-arm 9 which were reached during the calibration process, so that the projection geometries detected in the calibration process can be used for reconstructing 3D images.

The inventive X-ray device has been described above on the basis of a mobile C-arm X-ray apparatus 1. However, the inventive X-ray device does not necessarily have to be a C-arm X-ray device, but can be a different type of mobile X-ray device.

Moreover, the X-ray device need not offer all of the adjustment possibilities for the X-ray system as are described for the C-arm X-ray apparatus 1.

In order to enable a reproducible displacement movement of the X-ray system, the C-arm X-ray apparatus 1 need not necessarily use both a digitally controlled drive and compensation components. Rather, only a digitally controlled drive or only the first or second compensation components may be sufficient in order to achieve a reproducible displacement movement of the X-ray system.

Although various minor modifications might be suggested by those skilled in the art, it should be understood that my wish to embody within the scope of the patent warranted hereon all such modifications as reasonably and properly come with the scope of my contribution to the art.

I claim as my invention:

1. A mobile X-ray apparatus comprising:

an X-ray system comprising an X-ray source and a planar X-ray detector;

a displacement arrangement for displacing said X-ray system relative to an examination subject for picking up a series of 2D projections of said subject online, said X-ray system and said displacement arrangement being susceptible to mechanical instabilities;

a computer supplied with said 2D projections for reconstructing at least one 3D image of said subject therefrom; and said displacement arrangement including means for assuring a reproducible displacement movement of said X-ray system so that respective projection geometries required for reconstructing said 3D image are determined offline in a calibration process prior to picking up said series of 2D projections of said subject online.

2. A mobile X-ray apparatus as claimed in claim 1 wherein said means for assuring a reproducible displacement movement comprise a digitally controlled drive for effecting said displacement movement.

3. A mobile X-ray apparatus as claimed in claim 2 wherein said drive comprises a pulse motor.

4. A mobile X-ray apparatus as claimed in claim 1 wherein said X-ray system includes a carrier on which said X-ray source and said X-ray detector are mounted, and wherein said displacement arrangement includes a support on which said carrier is mounted and a holding device having a holding device axis so that said support is displaceable along said axis and rotatable around said axis relative to said holding device, and wherein said means for assuring a reproducible displacement movement comprise compensation components exhibiting a defined effective direction for interacting between said support and said holding device to compensate for any mechanical play between said support and said holding device.

5. A mobile X-ray apparatus as claimed in claim 4 further comprising a lifting device connected to said holding device for height-adjustment of said holding device, said lifting device comprising at least two lifting device elements which are movable relative to each other to effect height-adjustment of said holding device, and wherein said means for assuring a reproducible displacement movement comprise further compensation elements exhibiting a defined effective direction for interacting between said lifting device elements for compensating for any mechanical play between said lifting device elements.

6. A mobile X-ray apparatus as claimed in claim 5 wherein said compensation elements and said additional compensation elements are selected from the group consisting of locking elements and clamping elements.

7. A mobile X-ray apparatus as claimed in claim 4 wherein said carrier is a C-arm.

8. A method for determination of projection geometries in a mobile X-ray apparatus, said mobile X-ray apparatus having an X-ray system comprising an X-ray source and a planar X-ray detector, and a displacement arrangement connected to said X-ray system for displacing said X-ray system relative to a subject, said X-ray system and said displacement arrangement being susceptible to mechanical instabilities, and wherein said displacement arrangement comprises at least one displaceable component for effecting a displacement movement of said X-ray system in at least one displacement direction, said method comprising the steps of:

adjusting said at least one displacement component to a displacement position to effect said displacement movement of said X-ray system;

arranging a phantom relative to said X-ray system and penetrating said phantom with an X-ray beam emitted from said X-ray source, and detecting X-rays from said X-ray beam with said X-ray detector after said X-ray beam passes through said phantom;

picking up a series of 2D projections of said phantom online by moving said X-ray system relative to said phantom;

evaluating said series of 2D projections of said phantom offline for identifying respective projection geometries for each 2D projection in said series of 2D projections;

storing said projection geometries for said displacement position of said displaceable component; and obtaining a further series of 2D projections of said phantom if said displacement position of said displaceable component changes and evaluating said further series of 2D projections offline for identifying respective projection geometries for each 2D projection in said further series of 2D projections, and storing the respective projection geometries for said changed displacement position; and calculating a 3D image of said subject online using said stored projection geometries of said 2D projections in said series of 2D projections and, if present, using the stored projection geometries of the 2D projections in said further series of 2D projections.

9. A method as claimed in claim 8 wherein said X-ray system comprises a carrier on which said X-ray source and said X-ray detector are mounted, and wherein said displacement arrangement includes a support on which said carrier is mounted and a holding device having a holding device axis in which said support is mounted for movement around and along said holding device axis and a lifting device connected to said holding device for height-adjustment of said holding device, and wherein said displaceable component comprises at least one of said carrier, said support, said holding device and said lifting device.

* * * * *